US00PP30218P2

(12) United States Plant Patent
Koning

(10) Patent No.: US PP30,218 P2
(45) Date of Patent: Feb. 19, 2019

(54) ***DIANTHUS* PLANT NAMED 'KOND1060K1'**

(50) Latin Name: *Dianthus hybrida*
Varietal Denomination: KonD1060K1

(71) Applicant: Geu Koning, Westerbork (NL)

(72) Inventor: Geu Koning, Westerbork (NL)

( * ) Notice: Subject to any disclaimer, the term of this patent is extended or adjusted under 35 U.S.C. 154(b) by 0 days.

(21) Appl. No.: 15/732,312

(22) Filed: Oct. 23, 2017

(51) Int. Cl.
*A01H 5/02* (2018.01)

(52) U.S. Cl.
USPC ..... Plt./279

(58) Field of Classification Search
USPC ..... Plt./272, 279
See application file for complete search history.

*Primary Examiner* — Susan McCormick Ewoldt
(74) *Attorney, Agent, or Firm* — C. A. Whealy

(57) ABSTRACT

A new and distinct cultivar of *Dianthus* plant named 'KonD1060K1', characterized by its compact, low-growing, uniformly mounding and upright to outwardly spreading plant habit; dense and bushy appearance; silvery green-colored leaves; freely and remontant flowering habit; white-colored single flowers with purple-colored central ring; vernalization treatment not required for flowering; and good container and garden performance.

2 Drawing Sheets

Botanical designation: *Dianthus hybrida*.
Cultivar denomination: 'KonD1060K1'.

CROSS-REFERENCED TO CLOSELY-RELATED APPLICATION

Title: *Dianthus* Plant Named 'KonD1060K3'
Applicant: Geu Koning
Filed: Concurrently with U.S. Plant patent application Ser. No. 15/732,311

BACKGROUND OF THE INVENTION

The present invention relates to a new and distinct cultivar of *Dianthus* plant, botanically known as *Dianthus hybrida*, grown commercially as a container and garden plant and hereinafter referred to by the name 'KonD1060K1'.

The new *Dianthus* plant is a product of a planned breeding program conducted by the Inventor in Westerbrok, The Netherlands. The objective of the breeding program is to create new hardy *Dianthus* plants with remontant flowering habit with good container and garden performance.

The new *Dianthus* plant originated from a cross-pollination in May, 2009 of a proprietary selection of *Dianthus hybrida* identified as code number D917, not patented, as the female, or seed, parent with a proprietary selection of *Dianthus hybrida* identified as code number D900, not patented, as the male, or pollen, plant. The new *Dianthus* plant was discovered and selected by the Inventor in July, 2010 as a single flowering plant from within the progeny of the stated cross-pollination in a controlled environment in Westerbrok, The Netherlands.

Asexual reproduction of the new *Dianthus* plant by vegetive terminal cuttings propagated in a controlled greenhouse environment in Chicago, Ill. since September, 2010 has shown that the unique features of this new *Dianthus* plant are stable and reproduced true to type in successive generations of asexual reproduction.

SUMMARY OF THE INVENTION

Plants of the new *Dianthus* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'KonD1060K1'. These characteristics in combination distinguish 'KonD1060K1' as a new and distinct *Dianthus* plant:

1. Compact, low-growing, uniformly mounding and upright to outwardly spreading plant habit; dense and bushy appearance.
2. Silvery green-colored leaves.
3. Freely and remontant flowering habit.
4. White-colored single flowers with purple-colored central ring.
5. No vernalization requirement for flowering.
6. Good container and garden performance.

Plants of the new *Dianthus* differ primarily from plants of the female parent selection in the following characteristics:

1. Plants of the new *Dianthus* are not as vigorous as plants of the female parent selection.
2. Plants of the new *Dianthus* have smaller flowers than plants of the female parent selection.
3. Flowers of plants of the new *Dianthus* are more fringed than flowers of plants of the female parent selection.
4. Plants of the new *Dianthus* flower more consistently than plants of the female parent selection.

Plants of the new *Dianthus* differ primarily from plants of the male parent selection in the following characteristics:

1. Leaves of plants of the new *Dianthus* are more silvery green than leaves of plants of the male parent selection.
2. Plants of the new *Dianthus* and the male parent selection differ in flower color as plants of the male parent selection have light red purple-colored flowers without a central ring.

Plants of the new *Dianthus* differ primarily from plants of *Dianthus hybrida* 'KonD1060K3', disclosed in U.S. Plant Patent filed concurrently, in the following characteristics:

1. Plants of the new *Dianthus* are shorter than plants of 'KonD1060K3'.
2. Flowers of plants of the new *Dianthus* are smaller than flowers of plants of 'KonD1060K3'.
3. Plants of the new *Dianthus* and 'KonD1060K3' differ in flower color as plants of 'KonD1060K3' have light red purple-colored flowers.

Plants of the new *Dianthus* can also be compared to plants of *Dianthus caryophyllus* 'Kahori', not patented. In side-by-side comparisons, plants of the new *Dianthus* differ primarily from plants of 'Kahori' in the following characteristics:

1. Leaves of plants of the new *Dianthus* are more silvery green than leaves of plants of 'Kahori'.
2. Plants of the new *Dianthus* and 'Kahori' differ in flower color as plants of 'Kahori' have red purple-colored flowers without a central ring.

BRIEF DESCRIPTION OF THE PHOTOGRAPHS

The accompanying photographs illustrate the overall appearance of the new *Dianthus* plant showing the colors as true as it is reasonably possible to obtain in colored reproductions of this type. Colors in the photographs may differ slightly from the color values cited in the detailed botanical description which accurately describe the colors of the new *Dianthus* plant.

The photograph on the first sheet is a side perspective view of a typical flowering plant of 'KonD1060K1' grown in a container.

The photograph on the second sheet is a close-up view of a typical flowering plant of 'KonD1060K1'.

DETAILED BOTANICAL DESCRIPTION

Plants used in the aforementioned photograph and following observations and measurements were grown during the winter and spring in one-gallon containers in a glass-covered greenhouse in Elburn, Ill. and under cultural practices typical of commercial container *Dianthus* production. During the final production phase of the plants, day temperatures ranged from 18° C. to 21° C. and night temperatures ranged from 13° C. to 16° C. Plants were pinched two times during the propagation phase and were eight months old when the photographs and description were taken. In the following description, color references are made to The Royal Horticultural Society Colour Chart, 2007 Edition, except where general terms of ordinary dictionary significance are used.

Botanical classification: *Dianthus hybrida* 'KonD1060K1'.

Parentage:

*Female, or seed, parent*.—Proprietary selection of *Dianthus hybrida* identified as code number D917, not patented.

*Male, or pollen, parent*.—Proprietary selection of *Dianthus hybrida* identified as code number D900, not patented.

Propagation:

*Type*.—By vegetative terminal cuttings.

*Time to initiate roots, summer*.—About one week at temperatures ranging from 20° C. to 21° C.

*Time to initiate roots, winter*.—About two weeks at temperatures about 20° C. to 21° C.

*Time to produce a rooted young plant, summer and winter*.—About six to seven weeks at temperatures ranging from 7° C. to 16° C.

*Root description*.—Fine, fibrous; white in color, actual color of the roots dependent on substrate composition, water quality, fertilizer, substrate temperature and age of roots.

*Rooting habit*.—Freely branching; medium density.

Plant description:

*Plant and growth habit*.—Herbaceous perennial, typically grown as a container and garden plant; compact, low-growing, uniformly mounding, upright to outwardly spreading plant habit; moderately vigorous growth habit.

*Plant height, soil level to top of foliar plane*.—About 10 cm.

*Plant height, soil level to top of floral plane*.—About 12 cm.

*Plant diameter or spread*.—About 29 cm.

*Lateral branches*.—Branching habit: Freely basal branching habit with numerous primary lateral stems; each primary lateral stem with secondary lateral stems potentially forming at every node. Length, primary lateral stems: About 12 cm. Length, secondary lateral stems: About 5 cm. Diameter, primary lateral stems: About 2 mm. Diameter, secondary lateral stems: About 1 mm. Internode length, proximally: About 1 cm. Strength: Strong, flexible. Aspect, primary lateral stems: Outward then curving upright. Aspect, secondary lateral stems: About 30° from primary lateral stem axis. Cross-section: Round, solid. Texture and luster: Smooth, glabrous; matte. Color: Close to N137A; thin waxy cuticle, close to 189A.

Leaf description:

*Arrangement*.—Opposite, simple; sessile.

*Length*.—About 5.2 cm.

*Width*.—About 4 mm.

*Shape*.—Lanceolate.

*Apex*.—Narrowly acute.

*Base*.—Attenuate; decurrent.

*Margin*.—Entire.

*Texture and luster, upper and lower surfaces*.—Smooth, glabrous; matte.

*Venation pattern*.—Parallel.

*Color*.—Developing leaves, upper surface: Close to 146A. Developing leaves, lower surface: Close to 146B. Fully expanded leaves, upper surface: Close to N137A; thin waxy cuticle, close to 189A; venation, close to N137A. Fully expanded leaves, lower surface: Close to N137B; thin waxy cuticle, close to 189A; venation, close to N137B.

Flower description:

*Flower form and flowering habit*.—Terminal and axillary single flowers arranged singly or in pairs; freely flowering habit with numerous flowers developing during the flowering season; flowers face mostly upright to slightly outwardly.

*Natural flowering season*.—Consistent remontant flowering habit from the early spring until the autumn in northern Illinois; plants do not require a vernalization treatment to initiate flowering.

*Fragrance*.—Fragrant; clove-like, sweet.

*Flower buds*.—Length: About 1.4 cm. Diameter: About 3 mm. Shape: Oblong; styles not extruded. Texture and luster: Smooth, glabrous; matte. Color: Close to 144A.

*Flower diameter*.—About 3.2 cm.

*Flower depth*.—About 2 cm.

*Petals*.—Quantity and arrangement: Five petals arranged in a single whorl. Length: About 3.3 cm. Width: About 1.5 cm; at the base, about 1 mm. Shape: Spatulate, fan-shaped. Apex: Praemorse. Base: Elongated, tapering to a point. Margin: Entire. Texture and luster, upper and lower surfaces: Smooth, glabrous; velvety; matte. Color: When opening, upper surface: Close to NN155C to NN155D; central ring, close to N78A. When opening, lower surface: Close to NN155D. Fully opened, upper surface: Close to NN155C to NN155D; central ring, close to N78A; at the base, close to 145C to 145D; throat, close to NN155C to NN155D; venation, similar to lamina; color does not fade with development. Fully opened, lower surface: Close to NN155D; tube, close to 145C to 145D; venation, similar to lamina; color does not fade with development.

*Sepals*.—Quantity and arrangement: Five sepals arranged in a single whorl; proximal 75% portion of the sepals are fused into a campanulate-shaped calyx. Length: About 1.8 cm. Sepal width, at base of "free" portion: About 3 mm. Shape: Oblong. Apex: Acute. Margin: Entire. Texture and luster, upper and lower surfaces: Smooth, glabrous; matte. Color, inner surface: Close to 144A to darker than 144A. Color, outer surface: Close to 146A.

*Peduncles*.—Length: About 5 cm. Diameter: About 1 mm. Strength: Strong, flexible and wiry. Aspect: Erect to about 45° from vertical. Texture and luster: Smooth, glabrous; matte. Color: Close to N137A; thin waxy cuticle, close to 189A.

*Pedicels* (*when flowers arranged in pairs*).—Length: About 2 cm to 3 cm. Diameter: About 1 mm. Strength: Strong, flexible and wiry. Aspect: About 45° from the peduncle axis. Texture and luster: Smooth, glabrous; matte. Color: Close to N137A; thin waxy cuticle, close to 189A.

*Reproductive organs*.—Stamens: Quantity: About five stamens per flower. Filament length: About 2.5 mm. Filament color: Close to NN155C. Anther length: About 1 mm. Anther shape: Oblong. Anther color: Close to 10D. Pollen: None observed. Pistils: Quantity: About two per flower. Pistil length: About 2.2 cm. Stigma shape: Pointed, curled. Stigma color: Close to NN155C. Style length: About 1.25 cm. Style color: Close to NN155C. Ovary shape: Oblong. Ovary texture: Smooth, glabrous. Ovary color: Close to 144A to 144B. Fruits and seeds: Fruit and seed development have not been observed on plants of the new *Dianthus* to date.

Disease & pest resistance: Plants of the new *Dianthus* have not been observed to be resistant to pathogens and pests common to *Dianthus* plants.

Garden performance: Plants of the new *Dianthus* have been observed to have good garden performance and to tolerate wind, rain and to be suitable for USDA Hardiness Zones 5a to 9a.

It is claimed:

1. A new and distinct *Dianthus* plant named 'KonD1060K1' as illustrated and described.

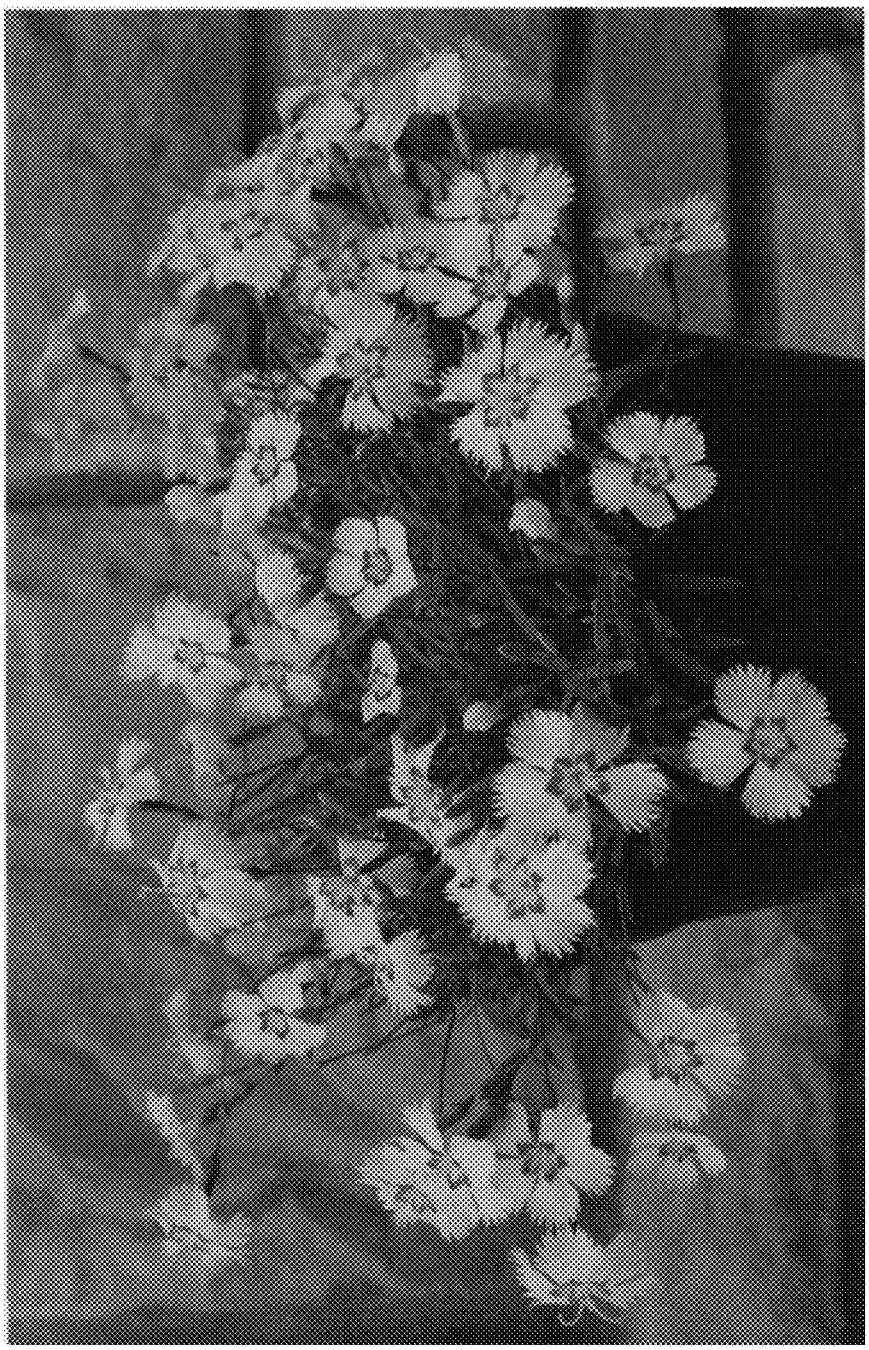

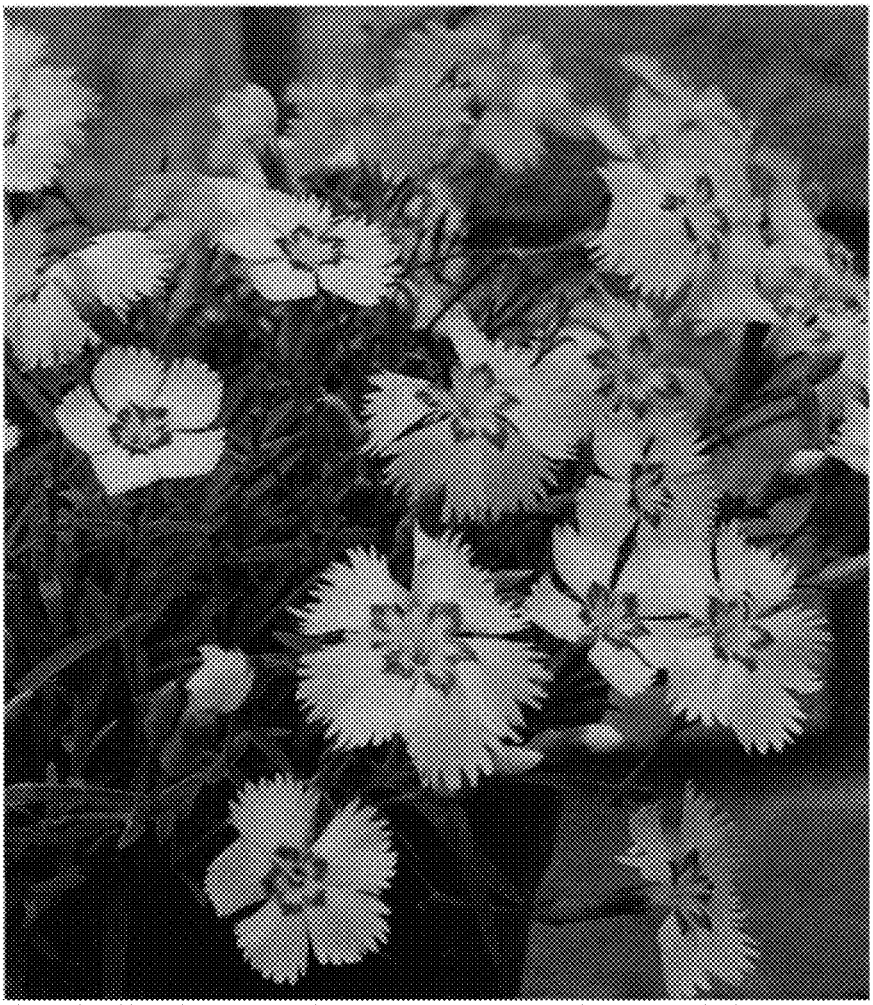

* * * * *